(12) United States Patent
Pitts Singer et al.

(10) Patent No.: US 9,301,521 B2
(45) Date of Patent: Apr. 5, 2016

(54) BEE ATTRACTANTS

(71) Applicants: United States of America, as represented by the Secretary of Agriculture, Washington, DC (US); AgPollen LLC, Ceres, CA (US)

(72) Inventors: Theresa Pitts Singer, Logan, UT (US); William P. Kemp, Fargo, ND (US); David Moreland, St. Helena, CA (US); Steve Peterson, Visalia, CA (US); James S. Buckner, Brunswick, ME (US); Marcia M. Hagen, Fargo, ND (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/200,599

(22) Filed: Mar. 7, 2014

(65) Prior Publication Data
US 2014/0271536 A1 Sep. 18, 2014

Related U.S. Application Data

(60) Provisional application No. 61/779,290, filed on Mar. 13, 2013.

(51) Int. Cl.
*A01N 37/02* (2006.01)
(52) U.S. Cl.
CPC ..................... *A01N 37/02* (2013.01)
(58) Field of Classification Search
None
See application file for complete search history.

(56) References Cited

U.S. PATENT DOCUMENTS

| | | | | |
|---|---|---|---|---|
| 3,976,588 A * | 8/1976 | McLaughlin | ............ | 34/283 |
| 8,053,464 B2 | 11/2011 | Quinn et al. | | |
| 8,282,952 B2 | 10/2012 | Smit | | |
| 2003/0118527 A1* | 6/2003 | Jager | ............ | A61K 8/0295 424/59 |
| 2013/0210823 A1* | 8/2013 | Fougeroux | ............ | 514/242 |

FOREIGN PATENT DOCUMENTS

| | | |
|---|---|---|
| WO | WO 02/067914 A1 | 9/2002 |
| WO | WO 2006/134377 A1 | 12/2006 |

OTHER PUBLICATIONS

Gettyimages, webpage at gettyimages.com [retrieved on Sep. 10, 2015], retrieved from the Internet: <URL: http://www.gettyimages.com/detail/news-photo/beekeepers-put-royal-jelly-into-an-artificial-comb-to-news-photo/52595283>, 2005.*
Webpage at e2121.com [retrieved on Sep. 10, 2015], retrieved from the Internet: <URL: http://www.e2121.com/food_db/viewherb.php3?viewid=480&setlang=>, publication date of Jul. 26, 2011.*
Cyr, "The Buzz About Bees" a webpage at www.masonbeehomes.com [retrieved on Sep. 10, 2015], retrieved from the Internet, publication date of May 5, 2006, <URL: http://web.archive.org/web/20060505140857/http://www.masonbeehomes.com/the_buzz_about_bees.php>.*
Issacs, "The Unforeseen Dangers of Coconut Oil Tanning Lotion (humor)", an article from www.naturalnews.com [retrieved Sep. 10, 2015], <URL: http://www.naturalnews.com/z023196_oil_tanning_water.html>, published May 9, 2008.*
Artz, Derek R. et al., "Nesting site density and distribution affect Osmia lignaria (Hymenoptera: Megachilidae) reproductive success and almond yield in a commercial orchard", (2013) Insect Conservation and Diversity 6:175-724.
Bosch, Jordi, William P. Kemp and Stephen S. Peterson, "Management of Osmia lignaria (Hymenoptera: Megachilidae) Populations for Almond Pollination: Methods to Advance Bee Emergence", (2000) Environmental Entomology 29(5):874-883.
Bosch, Jordi and William P. Kemp, "How to Manage the Blue Orchard Bee As an Orchard Pollinator", (2001) Sustainable Agriculture Network Handbook Series, Book 5, pp. 1-88.
Bosch, Jordi, William P. Kemp and Glen E. Trostle, "Bee Population Returns and Cherry Yields in an Orchard Pollinated with Osmia lignaria (Hymenoptera: Megachilidae)", (2006) Journal of Economic Entomology 99(2):408-413.
Conrad, Taina et al, "Female choice in the red mason bee, Osmia rufa (L.) (Megachilidae)", (2010) Journal of Experimental Biology 213:4065-4073.
Gruber, Bernd et al., "On managing the red mason bee (*Osmia bicornis*) in apple orchards", (2011) Apidologie 42:564-576.
Guedot, Christelle et al., "Olfactory cues and nest recognition in the solitary bee Osmia lignaria", (2006) Physiological Entomology 31:110-119.
Maccagnani, Bettina et al., "Osmia cornuta management in pear orchards", (2007) Bulletin of Insectology 60 (1):77-82.
Pitts Singer, Theresa, "Examination of 'pollen balls' in nests of the alfalfa leafcutting bee, *Megachile rotundata*", (2004) Journal of Apicultural Research 43(2):40-46.
Pitts Singer, Theresa, "Olfactory Response of Megachilid Bees, *Osmia lignaria, Megachile rotundata*, and *M. pugnata*, to Individual Cues from Old Nest Cavities", (2007) Environmental Entomology 36(2):402-408.
Rightmeyer, Molly G., Terry Griswold, Michael S. Arduser, "A review of the non-metallic Osmia (Melanosmia) found in North America, with additional notes on palearctic Melanosmia (Hymenoptera, Megachilidae)", (2010) ZooKeys 60:37-77, doi:10.38971zookeys.60.484.
Sekita, Norio, "Managing Osmia cornifrons to Pollinate Apples in Aomori Prefecture, Japan", (2001) Proceedings 8th Pollination Symposium—Acta Horticulturae 561:303-307.
Torchio, P.F.,"Field Experiments with Osmia lignaria propinqua Cresson as a Pollinator in Almond Orchards: III, 1977 Studies (Hymenoptera: Megachilidae)", (1982) Journal of the Kansas Entomological Society 55(1):101-116.
Torchio, P.F.,"Field Experiments with the Pollinator Species, Osmia lignaria propinqua Cresson, in Apple Orchards: IV, 1978 Studies (Hymenoptera: Megachilidae)", (1984) Journal of the Kansas Entomological Society 57(4):689-694.
Torcho, P. F., "Field Experiments with the Pollinator Species, Osmia lignaria propincua Cresson, in Apple Orchards: V (1979-1980), Methods of Introducing Bees, Nesting Success, Seed Counts, Fruit Yields (Hymenoptera: Megachilidae)", (1985) Journal of the Kansas Entomological Society 58(3):448-464.
Buckner, James S., "Cuticular lipids of female solitary bees, Osmia lignaria Say and Megachile rotundata (F.) (Hymenoptera: Megachilidae)", (2009) Comparative Biochemistry and Physiology, Part B 153:200-205.

* cited by examiner

Primary Examiner — Robert T Crow
Assistant Examiner — John P Nguyen
(74) Attorney, Agent, or Firm — David L. Marks; John D. Fado; Lesley Shaw

(57) ABSTRACT

Chemical attractants to *Osmia lignaria* and other bees are provided herein along with methods of using the attractants.

4 Claims, 5 Drawing Sheets

BEE ATTRACTANTS

CROSS REFERENCE TO RELATED APPLICATIONS

This application claims priority to U.S. Patent Application 61/779,290 filed Mar. 13, 2013.

BACKGROUND OF INVENTION

1. Field of Invention

This invention relates to attractants for bees in the genus *Osmia*, particularly *Osmia lignaria*, the blue orchard bee. The attractants can be useful for encouraging the bees to return to nesting structures and to make a nest in nesting structures. The invention also relates to a method for reducing dispersal of *Osmia* spp. by applying the attractants to an object or area. The invention also relates to a method of attracting *Osmia* spp. to an artificial nest site by applying the attractants to the artificial nest site.

2. Prior Art Description

More than ninety crops in the United States are pollinated by the European honey bee, *Apis mellifera*. The recent concern for honey bee health and the growing demand for more bees have increased interest in pollination with non-honey bee species. In fact, other bees are now being used and are greatly beneficial to certain crops. For example, *Megachile rotundata*, the alfalfa leafcutting bee, is a commercial pollinator for alfalfa, canola, trefoil and carrot seed. *Osmia lignaria* is a native, solitary species and an excellent pollinator of almonds, cherries, apples, and pears (Torchio, *Proc. Ent. Soc. Ont.* 118:111-124 (1987); Torchio, *Environ. Entomol.* 19:1649-1656 (1990); Bosch and Kemp, *How to Manage the Blue Orchard Bee as an Orchard Pollinator*, Sustainable Agriculture Network, National Agricultural Library; Beltsville, Md. (2001)). In fact, studies have shown that use of *O. lignaria* as a pollinator can increase yields over honey bee pollination in almonds, apples, and cherries (Torchio (1987); Torchio, *J. Kansas Entomol. Soc.* 58:448-464 (1985); Kuhn and Ambrose, *J. Kansas Ent. Soc.* 57:169-180 (1984); Bosch and Kemp, *Bee World* 80(4):163-173 (1999); and Bosch, et al., *J. Econ. Entomol.* 99(2):408-413 (2006)). Furthermore, *O. lignaria* females forage and pollinate under cloudy skies and at lower temperatures than most other bees and rarely sting.

Management systems for cavity-nesting bees are being developed for use in crop pollination. *Osmia* spp. are of particular interest because some species, e.g., *O. lignaria, O. cornuta, O. cornifrons*, and *O. bicornis*, emerge in the early spring and can be used specifically for fruit and nut production of spring-flowering crops such as almonds, apples, cherries, and blueberries (Bosch and Kemp (1999); Bosch and Kemp (2001); Sekita, et al., *Acta Horticulturae* 561:303-307 (2001), Bosch, et al. (2006); Maccagnani, et al., *Bulletin of Insectology* 60(1):77-82 (2007), Gruber, et al., *Apidologie* 42(5):564-576 (2011), Artz, et al., *Insect Conserv. Diver.* 6:715-724 (2013)). These bees are holarctic in distribution (Michener, *The Bees of the World*, $2^{nd}$ ed., Johns Hopkins U. Press (2007); Rightmeyer, et al., *ZooKeys* 60:37-77 (2010)).

Several difficulties exist in commercially managing *O. lignaria*. One difficulty is that the bees tend to disperse from their release site (as much as 50%) (Torchio 1982. *J. Kansas Entomol. Soc.* 55:101-116; Torchio 1984. *J. Kansas Entomol. Soc.* 57:689-694, Stanley, et al. 2011). Mortality of bees or their larva in previously used nesting structures is another barrier to commercial management of *O. lignaria* and other *Osmia* spp. under commercial development. Previously used nesting structures may contain diseases, parasitoids, and pests that infect or prey on the bees or their larva and reduce the bee population in subsequent years (Bosch and Kemp, 2001; Pitts-Singer, *J. Apic. Res.* 43:40-46 (2004)). Mortality may possibly be reduced by the bee manager using new, clean cavities in the nesting structure (see, e.g., Bosch and Kemp, 2001); however, that may lead to an increase in bee dispersal, the previously mentioned difficulty.

One potential solution to these problems is to increase the "attractiveness" of the structure of a natural or artificial nest site, thereby increasing the pollinating efficiency and reproduction of the bee. If more bees remain in an orchard at the artificial nest sites, then they could pollinate more of the crop. Also, more bees could produce more brood that would be used during the following crop season. In a laboratory bioassay, it was demonstrated that *O. lignaria* females in a Y-tube respond significantly to empty female cocoons and also tend to respond to a chloroform:methanol extract of cocoons when exposed to the air passing over the cocoon or filter paper containing the cocoon extract (Pitts-Singer, *Environ. Entomol.* 36: 402-408 (2007)). However, the use of empty cocoons or crude cocoon extracts as attractants is undesirable. A predetermined chemical composition that can be reliably manufactured and reproduced, and that can offer a constant level of efficacy, may be a stronger attractant and cost less than using empty cocoons or crude extracts.

SUMMARY OF INVENTION

It is an object of this invention to have an attractant containing at least one of the following: decanoic acid, dodecanoic acid, tetradecanoic acid, or mixtures thereof.

It is an object of this invention to have an attractant for bees containing at least one of the following: decanoic acid, dodecanoic acid, tetradecanoic acid, or mixtures thereof. It is a further object of this invention that the attractant optionally contains a carrier.

It is an object of this invention to have an attractant containing at least one of the following: decanoic acid, dodecanoic acid, tetradecanoic acid, or mixtures thereof; and optionally a carrier. It is another object of this invention that the amount of decanoic acid, if present, ranges between approximately 1 ng to approximately 20 g, the amount of dodecanoic acid, if present, ranges between approximately 1 ng to approximately 20 g, and the amount of tetradecanoic acid, if present, ranges between approximately 1 ng to approximately 20 g.

It is an object of this invention to have an attractant containing at least one of the following: decanoic acid, dodecanoic acid, tetradecanoic acid, or mixtures thereof; and optionally a carrier. It is another object of this invention that the amount of decanoic acid, if present, ranges between approximately 0.2115 mg to approximately 2115.4 mg, the amount of dodecanoic acid, if present, ranges between approximately 0.0744 mg to approximately 744 mg, and the amount of tetradecanoic acid, if present, ranges between approximately 0.0033 mg to approximately 33 mg.

It is an object of this invention to have an attractant for bees containing at least one of the following: decanoic acid, dodecanoic acid, tetradecanoic acid, or mixtures thereof. It is a further object of this invention that the attractant optionally contains a carrier. It is another object of this invention that the attractant contains at least one pheromone that acts on *Osmia* spp.

It is an object of this invention to have an attractant for *Osmia* spp. containing at least one of the following: decanoic acid, dodecanoic acid, tetradecanoic acid, or mixtures thereof. It is a further object of this invention that the attractant optionally contains a carrier. It is another object of this invention that the attractant optionally contains hexyl decanoate, decyl dodecanoate, or mixtures thereof.

It is an object of this invention to have an attractant for *Osmia* spp. containing at least one of the following: decanoic acid, dodecanoic acid, tetradecanoic acid, or mixtures thereof. It is a further object of this invention that the attractant optionally contains a carrier which is ethyl alcohol.

It is an object of this invention to have an attractant for *Osmia* spp. containing at least one of the following: decanoic acid, dodecanoic acid, tetradecanoic acid, or mixtures thereof. It is a further object of this invention that the attractant optionally contains a carrier which is ethyl alcohol. It is another object of this invention that the carrier contains denatonium benzoate. It is a further object of the invention that the carrier contains tert-butyl alcohol.

It is an object of this invention to have an attractant for *Osmia* spp. containing a mixture of decanoic acid, dodecanoic acid, and tetradecanoic acid. It is a further object of this invention that the attractant optionally contains a carrier.

It is an object of this invention to have an attractant for *Osmia* spp. containing a mixture of decanoic acid, dodecanoic acid, and tetradecanoic acid; and optionally a carrier.

It is an object of this invention to have an attractant for *Osmia* spp. containing a mixture of decanoic acid, dodecanoic acid, and tetradecanoic acid. It is a further object of this invention that the attractant contains ethyl alcohol as a carrier.

It is an object of this invention to have an attractant for *Osmia* spp. containing a mixture of decanoic acid and dodecanoic acid; and optionally a carrier.

It is an object of this invention to have an attractant for *Osmia* spp. containing a mixture of decanoic acid and dodecanoic acid. It is a further object of this invention that the attractant contains ethyl alcohol as a carrier.

It is an object of this invention to have an attractant for *Osmia* spp. containing a mixture of decanoic acid and tetradecanoic acid; and optionally a carrier.

It is an object of this invention to have an attractant for *Osmia* spp. containing a mixture of decanoic acid and tetradecanoic acid. It is a further object of this invention that the attractant contains ethyl alcohol as a carrier.

It is an object of this invention to have an attractant for *Osmia* spp. containing a mixture of dodecanoic acid and tetradecanoic acid; and optionally a carrier.

It is an object of this invention to have an attractant for *Osmia* spp. containing a mixture of dodecanoic acid and tetradecanoic acid. It is a further object of this invention that the attractant contains ethyl alcohol as a carrier.

It is an object of this invention to have a method for attracting bees by applying an effective amount of an attractant to an object or area. It is a further object of the invention that the attractant contains decanoic acid, dodecanoic acid, tetradecanoic acid or a mixture thereof, and optionally a carrier. It is another object of this invention that the bees are *Osmia* spp.

It is an object of this invention to have a method for attracting bees by applying an effective amount of an attractant to an object or area. It is a further object of the invention that the attractant contains decanoic acid, dodecanoic acid, tetradecanoic acid or a mixture thereof, and optionally a carrier. It is another object of this invention that the bees are *O. lignaria, O. cornifrons, O. bucephala, O. aglaia, O. ribifloris, O. bruneri, O. cornuta*, and *O. bicornis*.

It is an object of this invention to have a method for attracting bees by applying an effective amount of an attractant to an object or area. It is a further object of the invention that the attractant is a mixture of decanoic acid, dodecanoic acid, and tetradecanoic acid. It is another object of the invention that the attractant optionally contains a carrier.

It is an object of this invention to have a method for attracting bees by applying an effective amount of an attractant to an object or area. It is an object of this invention that the attractant contains at least one of the following: decanoic acid, dodecanoic acid, tetradecanoic acid, or mixtures thereof; and optionally a carrier. It is another object of this invention that the amount of decanoic acid, if present, ranges between approximately 1 ng to approximately 20 g, the amount of dodecanoic acid, if present, ranges between approximately 1 ng to approximately 20 g, and the amount of tetradecanoic acid, if present, ranges between approximately 1 ng to approximately 20 g.

It is an object of this invention to have a method for attracting bees by applying an effective amount of an attractant to an object or area. It is a further object of the invention that the attractant contains one or more of the following chemicals: between approximately 0.2115 mg to approximately 2115.4 mg decanoic acid, between approximately 0.0744 mg to approximately 744 mg dodecanoic acid, and between approximately 0.0033 mg to approximately 33 mg tetradecanoic acid. It is another object of the invention that the attractant optionally contains a carrier.

It is an object of this invention to have a method for attracting bees by applying an effective amount of an attractant to an object or area. It is a further object of the invention that the attractant contains at least one of the following: decanoic acid, dodecanoic acid, tetradecanoic acid, or mixtures thereof; and optionally a carrier. It is another object of this invention that the amount of decanoic acid, if present, ranges between approximately 1 ng to approximately 20 g, the amount of dodecanoic acid, if present, ranges between approximately 1 ng to approximately 20 g, and the amount of tetradecanoic acid, if present, ranges between approximately 1 ng to approximately 20 g. It is another object of the invention that the attractant contains ethyl alcohol as a carrier.

It is an object of this invention to have a method for attracting bees by applying an effective amount of an attractant to an object or area. It is a further object of the invention that the attractant contains at least one of the following: decanoic acid, dodecanoic acid, tetradecanoic acid, or mixtures thereof; and optionally a carrier. It is another object of this invention that the amount of decanoic acid, if present, ranges between approximately 0.2115 mg to approximately 2115.4 mg, that the amount of dodecanoic acid, if present, ranges between approximately 0.0744 mg to approximately 744 mg, and that the amount of tetradecanoic acid, if present, ranges between approximately 0.0033 mg to approximately 33 mg. It is another object of the invention that the attractant contains ethyl alcohol as a carrier.

It is an object of this invention to have a method for attracting bees by applying an effective amount of an attractant to an object or area. It is a further object of the invention that the attractant contains at least one of the following: decanoic acid, dodecanoic acid, tetradecanoic acid, or mixtures thereof; and optionally a carrier. It is another object of this invention that the amount of decanoic acid, if present, ranges between approximately 1 ng to approximately 20 g, the amount of dodecanoic acid, if present, ranges between approximately 1 ng to approximately 20 g, and the amount of tetradecanoic acid, if present, ranges between approximately 1 ng to approximately 20 g. It is another object of the invention that the attractant contains ethyl alcohol as a carrier. It is another object of this invention that the bees are *Osmia* spp.

It is an object of this invention to have a method for attracting bees by applying an effective amount of an attractant to an object or area. It is a further object of the invention that the attractant contains at least one of the following: decanoic acid, dodecanoic acid, tetradecanoic acid, or mixtures thereof; and optionally a carrier. It is another object of this invention that the amount of decanoic acid, if present, ranges between approximately 0.21154 mg and approximately 2115.4 mg, the amount of dodecanoic acid, if present, ranges between approximately 0.0744 mg and approximately 744 mg, the amount of tetradecanoic acid, if present, ranges between approximately 0.0033 mg and approximately 33 mg, or a mixture thereof. It is another object of this invention that the bees are Osmia spp.

It is an object of this invention to have a method for attracting Osmia spp. by applying an effective amount of an attractant to an object or area. It is a further object of the invention that the attractant is a mixture of decanoic acid and dodecanoic acid. It is another object of the invention that the attractant optionally contains a carrier.

It is an object of this invention to have a method for attracting Osmia spp. by applying an effective amount of an attractant to an object or area. It is a further object of the invention that the attractant is a mixture of decanoic acid and dodecanoic acid. It is another object of the invention that the attractant contains ethyl alcohol as a carrier.

It is an object of this invention to have a method for attracting Osmia spp. by applying an effective amount of an attractant to an object or area. It is a further object of the invention that the attractant is a mixture of decanoic acid and tetradecanoic acid. It is another object of the invention that the attractant optionally contains a carrier.

It is an object of this invention to have a method for attracting Osmia spp. by applying an effective amount of an attractant to an object or area. It is a further object of the invention that the attractant is a mixture of decanoic acid and tetradecanoic acid. It is another object of the invention that the attractant contains ethyl alcohol as a carrier.

It is an object of this invention to have a method for attracting Osmia spp. by applying an effective amount of an attractant to an object or area. It is a further object of the invention that the attractant is a mixture of dodecanoic acid and tetradecanoic acid. It is another object of the invention that the attractant optionally contains a carrier.

It is an object of this invention to have a method for attracting Osmia spp. by applying an effective amount of an attractant to an object or area. It is a further object of the invention that the attractant is a mixture of dodecanoic acid and tetradecanoic acid. It is another object of the invention that the attractant contains ethyl alcohol as a carrier.

DETAILED DESCRIPTION OF THE INVENTION

Figure 1A:
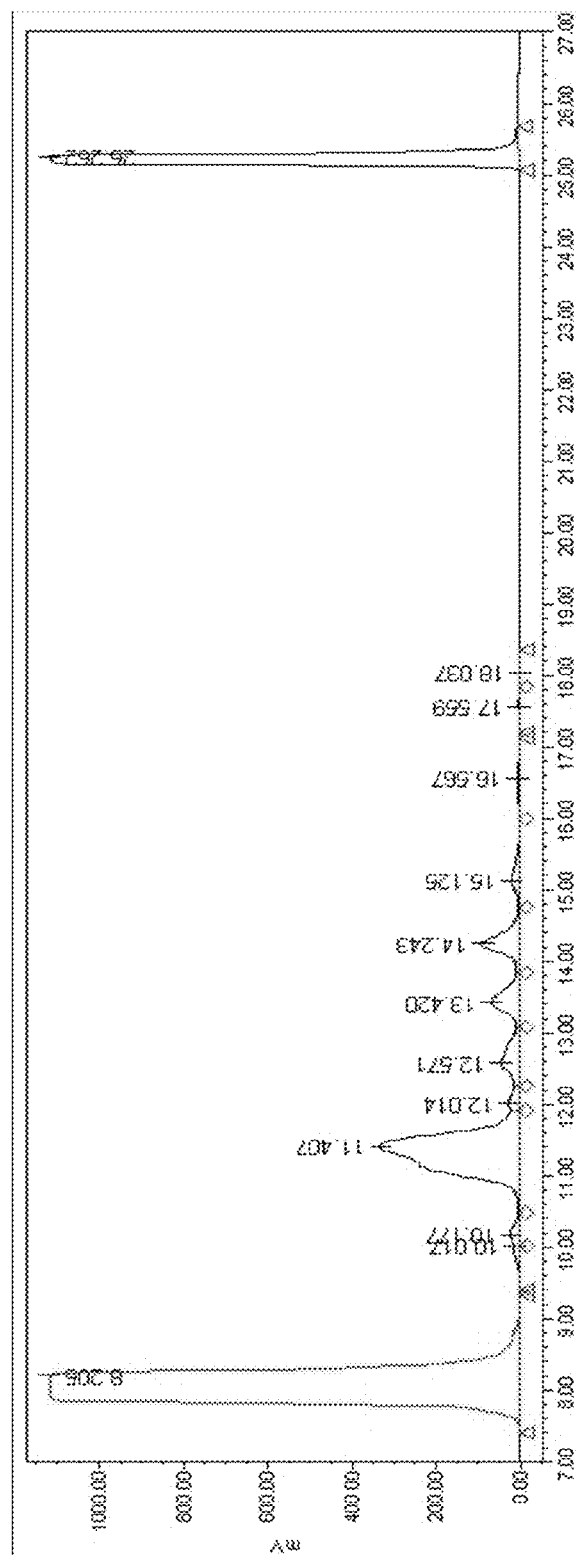
FIG. 1A is an HPLC-ELSD chromatogram of the chloroform extract of one female O. lignaria cocoon showing the time period when fractions were collected and obtained using the methods described in Example 1.

Commercial management of O. lignaria is useful for increasing pollination of certain crops, such as almonds, apples, cherries, and pears. Yet, difficulties in managing their populations exist, especially with attracting the bees to nesting structures or artificial nest sites. While old cocoons and crude extracts of old cocoons have been demonstrated to stimulate a response in female bees, use of the cocoons or crude extracts as attractants are not useful because, in part, of their cost and the potential for transmitting diseases. An attractant made from known, commercially produced chemicals can be cheaper to produce, more consistent in strength, and easier to use.

There is a need to have chemical attractants for Osmia spp. so that one can induce the bees to remain in an orchard or particular nest sites, so that one can induce Osmia spp. to make nests at particular nest sites, and lay eggs at particular nest sites. Chloroform ($CHCl_3$) extraction of cocoons is expensive and time consuming. Identifying specific chemical compositions that are attractants is desirable. This invention covers one such set of attractants and the methods of using the attractants.

The present invention relates to attractants and methods of attracting bees, in particular of the genus Osmia, and more particularly, O. lignaria to an object (an artificial nest site, an orchard, a natural nest site, etc.) or an area by treating the object or area with one or more of the attractants described herein. The term "bee" includes O. lignaria and other related bees that may be attracted to these attractants such as, but not limited to, O. bicornis, O. bucephala, O. cornifrons, O. aglaia, O. ribifloris, O. bruneri, and O. cornuta.

For the purposes of this invention, an "attractant" is a substance made from one or more chemicals or biological molecules that, when applied to an artificial nest site or other object, result in bees making a nest at the artificial nest site or overnighting at the artificial nest site or the object. The attractants for this invention are at least one of the following three fatty acids: decanoic acid, dodecanoic acid, and tetradecanoic acid. The attractant can contain at least two of these fatty acids or all three of these fatty acids. Decanoic acid, also known as capric acid, is a saturated fatty acid with a 10-carbon atom chain, having a molecular formula of $CH_3(CH_2)_8COOH$. Its CAS is 334-48-5. Dodecanoic acid, also known as lauric acid, is a saturated fatty acid with a 12-carbon atom chain, having a molecular formula of $CH_3(CH_2)_{10}COOH$. Its CAS is 143-07-7. Tetradecanoic acid, also called myristic acid, is a common saturated fatty acid with a 14-carbon atom chain with the molecular formula $CH_3(CH_2)_{12}COOH$. Its CAS is 544-63-8.

Compositions are disclosed for attracting Osmia spp. bees, both male and female bees, to artificial nest sites. In one embodiment, the compositions contain at least one of decanoic acid, dodecanoic acid, or tetradecanoic acid. However, in other embodiments, the attractant compositions can also contain two or three of these chemicals. In other embodiments, the compositions can include carriers and other chemicals as described in more detail herein. Further, methods for using compositions containing at least one of decanoic acid, dodecanoic acid, or tetradecanoic acid or containing at least two of these chemicals or all three of these chemicals, with or without carrier(s) or other chemicals to attract *Osmia* spp. bees to artificial nest sites are provided herein. Also, methods for using the attractants described herein to reduce the dispersal of *Osmia* spp. is also described herein.

Also disclosed are attractant compositions containing at least one of decanoic acid, dodecanoic acid, or tetradecanoic acid; or at least two of these chemicals, or all three of these chemicals useful for attracting blue orchard bees. The attractant compositions can also include other chemicals or compounds as described herein. Furthermore, this invention involves a method for attracting *Osmia* spp. by applying an effective amount of the attractant compositions of this invention to an artificial nest site, as well as a method for reducing dispersal of *Osmia* spp. by applying an effective amount of the attractant compositions of this invention to an artificial nest site.

The attractants may be applied to an object, such as an artificial nest site, or to an area, by spraying the attractant from an aerosol spray can, a pump spray bottle, a trigger spray bottle, wiping a liquid containing the attractants onto the object or area, etc. An aerosol can containing the attractants also includes a propellant so that the attractants can be released from the aerosol can.

The attractants of the present invention may be applied with a carrier (e.g., biologically or agronomically acceptable carrier). Non-limiting examples of suitable carriers are honey, glucose, sucrose, fructose, water, clay, cellulose-based materials, rubber materials, organic polymers, inorganic polymers, ethyl alcohol, methanol, butanol, plant-derived oils (palm, coconut, peanut, olive, sunflower, sorghum, canola, etc.), petroleum-based oils (mineral, petroleum, etc.), and animal-derived oils (caster, omega-3, squalene, etc.). The carrier may potentially include other compounds that assist in the suspension or dissolution of the attractants within the carrier such as, but not limited to, emulsifiers, surfactants, etc. In one embodiment, the carrier is ethyl alcohol. In another embodiment, the carrier is a combination of ethyl alcohol, tert-butyl alcohol and Bitrex® (denatonium benzoate) (Johnson Matthey Macfarlan Smith, Edinburgh, Scotland). The carrier, as used herein, excludes the bodies of *O. lignaria* and other *Osmia* spp., as well as the intact cocoons of *O. lignaria* and other *Osmia* spp. The attractants can be a liquid or a solid material. They can be applied to potential nesting areas, membranes, hollow fibers, cigarette filters, wood, plastic, gels, glass, metal, filter paper, artificial nest sites, natural nest sites, etc.

The amount of attractant used is, at a minimum, an effective amount. An effective amount is the minimum amount of attractant necessary to attract the animal of interest (*Osmia* spp.) to the treated area or object compared to the same area or object that is untreated. The precise amount needed will vary in accordance with the particular attractant used; the type of area or object that is treated with the attractant; the number of days of attractiveness needed; the environment in which the area or object is located; the animal that is being attracted; and the sex of that animal. One of ordinary skill in the art can easily determine the amount of attractant necessary to attract the desired animal, especially using the information contained herein.

In one embodiment, the effective amount of decanoic acid can range from approximately 1 ng to approximately 20 g. In another embodiment, the effective amount of decanoic acid can range from approximately 10 ng to approximately 2 g. In yet another embodiment, the effective amount of decanoic acid can range from approximately 100 ng to approximately 2 g. Alternatively, the amount of decanioc acid can range from approximately 50 ng to approximately 500 mg, or from approximately 100 ng to approximately 200 mg, or from approximately 200 ng to approximately 100 mg. These amounts of decanoic acid can be used by itself, or in combination with one or more of the other compounds disclosed herein.

In one embodiment, the effective amount of dodecanoic acid can range from approximately 1 ng to approximately 20 g. In another embodiment, the effective amount of dodecanoic acid can range from approximately 10 ng to approximately 2 g. In yet another embodiment, the effective amount of dodecanoic acid can range from approximately 100 ng to approximately 2 g. Alternatively, the amount of dodecanioc acid can range from approximately 50 ng to approximately 500 mg, or from approximately 100 ng to approximately 200 mg, or from approximately 200 ng to approximately 100 mg. These amounts of dodecanoic acid can be used by itself, or in combination with one or more of the other compounds disclosed herein.

In one embodiment, the effective amount of tetradecanoic acid can range from approximately 1 ng to approximately 20 g. In another embodiment, the effective amount of tetradecanoic acid can range from approximately 10 ng to approximately 2 g. In yet another embodiment, the effective amount of tetradecanoic acid can range from approximately 100 ng to approximately 2 g. Alternatively, the amount of dodecanioc acid can range from approximately 50 ng to approximately 500 mg, or from approximately 100 ng to approximately 200 mg, or from approximately 200 ng to approximately 100 mg. These amounts of tetradecanoic acid can be used by itself, or in combination with one or more of the other compounds disclosed herein.

In yet another embodiment, the effective amount of decanoic acid can range from approximately 0.21154 mg to approximately 2115.4 mg; the effective amount of dodecanoic acid can range from approximately 0.0744 mg to approximately 744 mg, and the effective amount of tetradecanoic acid can range from approximately 0.0033 mg to approximately 33 mg. In another embodiment, the effective amount of decanoic acid can range from approximately 2.1154 mg to approximately 211.54 mg, the effective amount of dodecanoic acid can range from approximately 0.744 mg to approximately 74.4 mg, and the effective amount of tetradecanoic acid can range from approximately 0.033 mg to approximately 3.3 mg. In a third embodiment, an effective amount of decanoic acid is approximately 21.154 mg; an effective amount of dodecanoic acid is approximately 7.44 mg, and an effective amount of tetradecanoic acid is approximately 0.33 mg.

An attractant may also optionally contain a known-in-the-art pheromone to assist in attracting the animal of interest. The pheromone should not substantially interfere with the attractants of this invention. Examples of possible pheromones include, but are not limited to, cuticular sex pheromone (male hydrocarbons) from *O. bicornis* (Conrad, et al., *J. Exp. Biol.* 213:4065-4073 (2010)); individual nest recognition cues from *O. lignaria* (Guédot, et al., *Physiol. Entomol.* 31:110-119 (2006)); or scents that some species of *Osmia* use to mark their nest entrances (see, e.g., Steinmann, E., *Bulletin de la Société Entomologique Suisse* 49:253-258 (1976); Raw, A., *The Entomologist* 111:79-87 (1992); and Rosner, B., *Chemische Kommunikation bei der Mauerbiene Osmia rufa (Megachilidae)*. MS thesis, University of Vienna (1994)). Other compounds may also be added to the attractants of the present invention, again, so long as the other compounds do not interfere with the attractants of the present invention. One of ordinary skill in the art can determine if another compound interferes with the attractants of this invention using the procedures and protocols set forth herein.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1

Purification and Identification of Chemicals in Cocoon Extracts

Parental *O. lignaria* are originally sourced from Utah, but emerged in California to produce progeny, from which cocoons are obtained after emergence in the subsequent year. Cocoons are placed in brown paper bags and then in plastic Ziploc® bags (SC Johnson, Racine, Wis.) and are stored at −5° C. until ready for processing. After warming to room temperature, contaminating frass, meconium and other debris are removed with forceps and an artist's brush prior to initiation of lipid extraction. For each set of extractions, 100 largely whole *O. lignaria* cocoons are submersed in 200 ml $CHCl_3$ for five minutes and then undergo a 30 second rinse with 25 ml $CHCl_3$. Following filtration through coarse filter paper (Fisherbrand® PN 09-790-14G (Thermo Fisher Scientific, Waltham, Mass.)), the solvent volume is reduced without heat using a rotary evaporator and a stream of nitrogen gas. Cocoon extract samples are layered with argon gas and stored at −5° C.

Figure 1B:
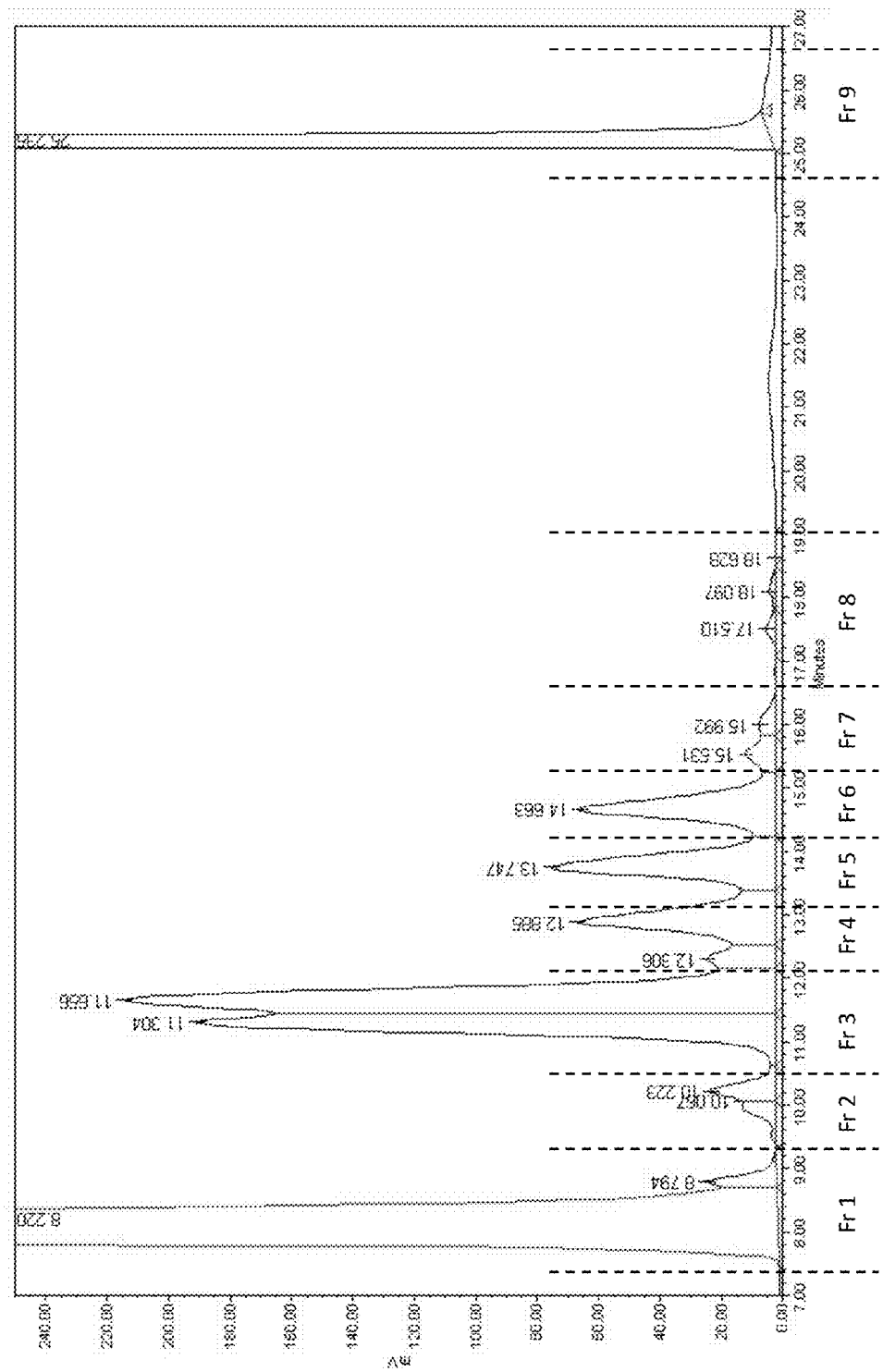
FIG. 1B is another typical HPLC-ELSD chromatogram magnified to show the relative size of peaks in the various Fractions 1-9 (Fr 1-9). Dotted lines delineate all peaks and retention times included in each fraction.

Prior to performing high performance liquid chromatography, cocoon extract samples are warmed to room temperature, and all traces of $CHCl_3$ are removed without heat using a stream of nitrogen gas. The resulting viscous oil is adjusted to 0.025 cocoon equivalents (CE)/µl with 99:1 hexane:acetic acid, sonicated and filtered through a 17 mm 0.45 µm PTFE filter. One CE aliquots of the sample are fractionated using a Waters Model 2695 Separations Module (Waters Corp., Milford, Mass.) equipped with 2 LiChrospher® 100 Diol 5 µm 250 mm×4 mm ID HPLC columns (PN 79925DI-584, Agilent Technologies, Santa Clara, Calif.) plumbed in series and preceded by a 7 µm 15 mm×3.2 mm ID silica guard column in a Brownlee New Guard holder (Applied Biosystems PN 0715-0001 (Life Technologies, Carlsbad, Calif.)). The columns are equilibrated at 0.6 ml/minute and 30° C. with hexane. Initial conditions are held for 17 minutes and then are switched instantaneously to 84:15:1 hexane:isopropanol:glacial acetic acid while the flow rate increases linearly to 1 ml/minute over 1 minute. This condition is held for 7 minutes, and then switched back to 100% hexane instantaneously while the flow rate increases linearly over 1 minute to 1.5 ml/minute and is held for 36 minutes. The flow rate decreases to 0.6 ml/minute over 1 minute and is held for 3 more minutes before the next injection initiates. Column performance is monitored at least once every 24 hours with the Sedex (Model 55) evaporative light scattering detector (ELSD) (SEDERE, Alfortville Cedex, France) at room temperature (~23-28° C.) and $N_2$ (g) pressure of 2.0 bar. FIG. 1A is a full-scale view of HPLC-ELSD chromatogram of one cocoon extract obtained using these methods; FIG. 1B is the enlarged view of a selected portion of the same HPLC-ELSD chromatogram of one cocoon extract using these methods.

Column eluate from all other runs of the cocoon extract are collected between 7-27 minutes using a fraction collector. The fractions are pooled daily as listed below in Table 1 and shown in FIG. 1B. All solvents are dried at room temperature under a stream of nitrogen gas, and pooled fractions are stored at −5° C. each night. After 100 CEs are accumulated in the vials (approximately every 5 days), the samples are dissolved in ~3.5 ml $CHCl_3$, layered with Argon gas and are stored at −80° C.

TABLE 1

| Fraction # | Time Range (minutes) |
|---|---|
| 1 | 7.5–9.3 |
| 2 | 9.4–10.5 |
| 3 | 10.6–12.1 |
| 4 | 12.2–13.0 |
| 5 | 13.1–14.2 |
| 6 | 14.3–15.2 |
| 7 | 15.3–16.5 |
| 8 | 16.6–19.0 |
| 9 | 24.5–26.9 |

Example 2

Field Tests with Fractions

Fractions 1, 3, 4, 9, and a pool of Fractions 5, 6, 7, and 8 from the HPLC column are applied to separate filter papers so that each filter paper contains 5 CE. As a negative control, $CHCl_3$ is applied to its own filter paper. As a positive control, an unfractionated $CHCl_3$ extract of cocoon is applied to filter paper at 5 CE. Fraction 2 is not used because it contained very little material. Fractions 5, 6, 7, and 8 are combined together because of the small amount of material in the fractions.

Three field experiments are conducted using these filter papers containing cocoon extracts. One experiment conducted in an almond orchard in California, small, corrugated plastic box artificial nest sites (20×23×20 cm) are hung facing southeast in almond trees in an orchard with two bundles of 19 paper tubes in each artificial nest site. The tubes are sealed at the back with corks and are used by the bees as nesting cavities. The center tube contains a piece of filter paper containing the fractions or controls at 5 CE; the filter paper being inserted into a slot made with a razor blade in the cork at the back of the center tube. Bees are released from throughout the orchard at least 100 feet from the artificial nest sites. Treatment corks are replaced weekly. Nest sites are checked 3 to 4 times per week, and completed nests are removed and replaced with fresh tubes. Female counts are taken at night one week apart.

In an experiment in cages containing wildflowers in California, Fractions, 1, 3, 5-8 and 9 are used with $CHCl_3$ as the negative control. These fractions and negative control are applied to two pieces of filter paper containing the extracts, for a total of 10 CE. Modified half-gallon, paperboard milk cartons are used as artificial nest sites. The tops of the milk cartons are cut off, and remaining cartons are painted flat black. Each artificial nest site contains one bundle of 19 cardboard tubes, secured with Velcro. The artificial nest sites are mounted on metal posts, approximately 1 m above the ground and 1.2 m from each other, with the opening to the artificial nest sites facing east, in mesh cages (approx. 6×6×2 m). The cages are placed over a mix of blooming wildflowers (*Phacelia, Collinsia*, and *Nemophilia*) known to provide adequate resources for *O. lignaria* production. There are five cages, and the treatments are randomized within each cage. The two filter papers containing the fractions or control are placed at the front of the tubes with cable ties. Females and males are released into the cages until a total of 10-12 females are in each cage. Releases begin on Apr. 21, 2011, and nesting observations are made until May 26, 2011. Artificial nest sites are checked daily for the presence of pollen or females in the tubes using a head mounted surgical light. Once a female has chosen to initiate a nest in a tube (e.g., pollen is in the tube), both the tube and the bee are removed from the cage, and the tube is replaced with a fresh one. Newly emerged bees are added to each cage to maintain 10 to 12 females per cage as needed. Treated filter papers are changed weekly.

In a third experiment in an apple orchard in Utah, Fractions 1, 3, 5-8, and 9 are again tested, being applied to filter paper at 5 CE per filter paper. The negative control is again $CHCl_3$. Small, corrugated plastic box artificial nest sites (same as used for the experiment in an almond orchard above) are hung in apple trees with two bundles of 19 tubes in each artificial nest site. Two filter papers containing Fraction 1, 3, 5-8, or 9 (for 10 CE total) are attached to the front of tubes in each artificial nest site using cable ties. Filter papers treated with $CHCl_3$ (negative control) are similarly attached. The filter papers are replaced weekly. Each artificial nest site contains only one type of treatment. Artificial nest sites are placed in the orchard in four groups of five, with each artificial nest site opening faced southeast. Approximately 400 female and 800 male bees are released throughout the orchard at least 40 feet from the artificial nest sites. Artificial nest sites are checked daily for the presence of male and female bees and for completed nests. Completed nests are removed and are replaced with fresh tubes.

Based on the results of these studies, it is decided to investigate Fraction 9 further.

Example 3

Identification of Chemicals in Fraction 9

Gas chromatography mass-spectrometry (GC-MS) is performed to further identify the chemicals in each fraction. Individual lipid components are separated by capillary gas chromatography (GC), quantified by their flame ionization detector (FID) response, and identified by GC-MS. GC-FID analyses are performed using an Agilent 6890 gas chromatograph (Agilent Technologies, Santa Clara, Calif.) equipped with a temperature- and pressure-programmable on-column injector and a DB-1MS capillary column (J&W Scientific, Folsom, Calif.) (0.2 mm×12.5 m, 0.33 μm phase thickness). The column oven temperature program is 50° C. for 30 seconds, then increases to 225° C. at 25° C./minute, next increases to 340° C. at 10° C./minute and is held at this temperature until all peaks elute. Samples are introduced onto the column via a 2 m retention gap of uncoated, deactivated fused silica with the hydrogen carrier at 20 psig. After 30 seconds, the pressure is reduced to 7 psig, and then increased at 1 psi/minute to 30 psig where it is held until the end of the run.

GC-MS analyses are performed on a Hewlett Packard Model 5890A gas chromatograph (Agilent Technologies, Santa Clara, Calif.) equipped with a temperature- and pressure-programmable on-column injector and a 1 m retention gap, connected to a DB-1MS column (same dimensions as above) coupled to an HP 5970B quadrupole mass selective detector. The carrier gas was 0.75 ml/minute helium, programmed for constant flow. The initial oven temperature is held for 4 minutes, then programmed to increase to 320° C. at 4° C./minute and to hold at that temperature until all peaks elute. For analysis of Fractions 1-3, the initial oven temperature is 150° C.; for Fractions 4-8, the initial oven temperature is 125° C., and for Fraction 9 the initial oven temperature is 70° C. For all analyses, the inlet temperature is programmed to maintain a temperature 3° C. higher than the oven temperature throughout the run. The results of the GC-MS analysis of Fraction 9 are provided in Table 2.

TABLE 2

| | Fraction 9 | |
|---|---|---|
| Lipid Class | # of Peaks* | Percent Peak Area |
| n-alkanes | 0 | 0 |
| Me-branched alkanes | 0 | 0 |
| Alkenes | 0 | 0 |
| Wax esters | 0 | 0 |
| Free fatty acids | 16 | 98 |
| Sterols | 2 | 0 |
| TAGs | 2 | 0 |
| Unidentified peaks | 10 | 2 |
| Contaminant | 0 | 0 |
| Total | 30 | 100% |

*Trace components (<0.1% of peak area) remain uncounted.

Fraction 9, which is pooled fractions from 24.5-27.0 minutes retention on HPLC, is approximately 98% free fatty acids. Of these fatty acids, saturated fatty acids, both even and odd chain lengths ranging from 10 to 24 are present with 10:0 being the most concentrated; however, chain length of 21 is not detected. Furthermore, Fraction 9 has unsaturated fatty acids containing carbon chain lengths fourteen and higher, and a small quantity of triacylglycerides (TAGs). Fraction 9 also contains small quantities of several compounds, the identities of which are not yet elucidated.

Example 4

Female Bee Attraction to Mixture of Chemicals Found in Cocoons

Five commercially available chemicals present in cocoons are assessed for attractiveness to *O. lignaria*. The chemicals and the quantity present in cocoons are contained in Table 3.

TABLE 3

| Class | Carbons | Chemical Name | μg/cocoon |
|---|---|---|---|
| Free Fatty Acid | 10:0 | decanoic acid | 105.77 |
| Free Fatty Acid | 12:0 | dodecanoic acid | 37.2 |
| Free Fatty Acid | 14:0 | tetradecanoic acid | 1.65 |
| Wax ester | 16:0 | hexyl decanoate | 0.008 |
| Wax ester | 22:0 | decyl dodecanoate | 0.8 |

Decanoic acid, dodecanoic acid and tetradecanoic acid are present in Fraction 9 of the cocoon and hexyl decanoate and decyl dodecanoate are present in Fraction 4 of the cocoon. Suterra (Bend, Oreg.) purchased decanoic acid, dodecanoic acid and tetradecanoic acid from a commercial supplier (TCI Americas, Portland, Oreg.) and synthesized hexyl decanoate and decyl dodecanoate (Suterra, Bend, Oreg.). The chemicals are very soluble in ethyl alcohol (99.9%), and do not precipitate out of solution. The chemicals in Table 3 are mixed with ethyl alcohol (Equistar Chemicals, LP, product SDA40B/200PF/DNB TBA/147600, Houston, Tex.) in the proportions provided in Table 3. The ethyl alcohol also contains tert-butyl alcohol (0.1% by weight) and denatonium benzoate or Bitrex® (0.001% by weight) (Johnson Matthey Macfarlan Smith, Edinburgh, Scotland). The five chemicals in Table 3 combined with the ethyl alcohol solution are hereinafter referred to as "Synthetic Blend." Suterra places the Synthetic Blend in an aerosol applicator (referred to hereinafter as "puffer" or "applicator") so that depressing the puffer's trigger once causes the puffer to emit 0.036 ml of the Synthetic Blend as a spray containing 10 CE of each chemical. Depressing the trigger ten times results in 100 CE of Synthetic Blend being released from the puffer. As a positive control, an extract of cocoons is made by soaking emerged cocoons in 95% ethanol (BioQuip Products, PN 1183, Rancho Dominguez, Calif.) for one month, and straining the liquid through filter paper. This extract includes fecal pellets and male cocoons and most likely includes some parts of dead bees. The filtered extract is placed in a 1 quart garden spray bottle with one trigger-pull yielding an equivalent of 2.6 cocoon equivalents.

Two field trials are conducted in California using the Synthetic Blend formulation and puffers described previously; one near Waterford (Stanislaus County) and the second near Lost Hills (Kern County). Grooved laminates of treated wood composite panel (Extira®, CMI, Chicago, Ill.) are constructed to form nesting cavities and are used in the Waterford study, and poplar laminates (Prairie Pollinating, Inc., Yorkton, Saskatchewan, Canada) are used similarly in the Lost Hill study. Each artificial nest site consists of nine grooved laminates, which makes an array of sixty-four holes. A plastic corrugated roof protects the artificial nest site from rain, and a plastic cable tie is used to attach the artificial nest site to a tree branch with the openings facing southeast. One of four experimental treatments is sprayed directly onto the front of each artificial nest site: (1) negative control (aerosol with ethyl alcohol (Equistar Chemical LP, product SDA40B/200PF/DNB TBA/147600, Houston, Tex.)) applied at the rate as used in treatment #3, (2) Synthetic Blend at 10 CE, (3) Synthetic Blend at 100 CE, and (4) filtered cocoon extract at approximately 10.4 CE as a positive control.

In the Waterford experiment, twenty-four artificial nest sites are hung on Nonpareil almond trees in a randomized complete block design with six replicates. Within a block, artificial nest sites are separated by a row of trees (thirty feet apart), and blocks are separated by six to eight rows (a minimum of 132 feet). On February 1, artificial nest sites are hung in the trees; on February 15, the first male and female cocoons are placed in the orchard; and on February 22, the artificial nest sites are treated with the negative control, positive control and Synthetic Blend. The weather from February 16 to February 21 is rainy and cool with high temperatures ranging from 48 to 56° F., and, thus, is not conducive to emergence of the bees or application of bee attractant and the controls. On March 14, the number of established female bees is close to statistical significance at the 0.10 level (F=2.37, df=3.19, P=0.103), with a strong indication that female bees prefer the 100 CE Synthetic Blend-treated artificial nest sites (see Table 4). Completed nests are counted three times in the field, and a final nest count is made once nesting is complete. There is no significant difference in completed nests among the treatments (F=0.49, df=3.19, P=0.69) (see Table 4).

TABLE 4

| Waterford almond orchard experiment | Females/replicate | Nests/replicate | Cells/replicate |
|---|---|---|---|
| Synthetic Blend (10 CE) | 6.7 ± 1.2 | 5.3 ± 2.93 | 57.2 ± 7.1 |
| Synthetic Blend (100 CE) | 9.2 ± 1.1 | 4.2 ± 2.09 | 74.3 ± 8.7 |
| Cocoon Extract (10.4 CE) | 5.8 ± 1.2 | 5.2 ± 1.51 | 60.2 ± 9.5 |
| Negative Control | 5.0 ± 1.3 | 3.2 ± 0.47 | 63.2 ± 14.6 |

In Lost Hills, forty artificial nest sites are hung in almond trees in ten replicates. Almond varieties in this orchard are Butte, Padre, and Fritz. Within a replicate, artificial nest sites are on adjacent trees, and the replicates are separated by 6 rows. Using two-way ANOVA, a significant difference exists among the treatments for completed nests (F=4.24, df=3.27, P=0.014). Significantly more nests are completed in artificial nest sites containing Synthetic Blend 100 CE compared to the negative control (Fisher's LSD) (see Table 5).

TABLE 5

| Lost Hills almond orchard experiment | Completed Nests/replicate |
|---|---|
| Synthetic Blend (10 CE) | 9.2 ± 2.0 |
| Synthetic Blend (100 CE) | 19.5 ± 3.7 |
| Cocoon Extract (10.4 CE) | 11.5 ± 1.8 |
| Negative Control | 8.5 ± 1.5 |

While the results differ slightly between the Waterford and Lost Hills experiments, 100 CE application of the Synthetic Blend is the best treatment for attracting nesting females. In the Waterford experiment, 100 CE Synthetic Blend applied to artificial nest sites increases established females by 1.8 fold and in the Lost Hills experiment, 100 CE Synthetic Blend applied to artificial nest sites increases completed nests by 2.3 fold.

Next, Synthetic Blend at 10 CE and 100 CE, filtered cocoon extract at 10.4 CE, and the negative control, all made as described above, are tested for attraction of *O. lignaria* females when applied to new, laminate artificial nest sites in five acre screenhouses planted with *Phacelia* in Ballico, Calif. and Lost Hills, Calif.

In Ballico, there are twelve replicates (for a total of 48 artificial nest sites) in a 5-acre propagation screenhouse. Each artificial nest site is attached to a wood post (spaced 35 feet from other posts). The blocks are laid out in the north-south direction. Three of the replicates have artificial nest sites made from treated wood composite panel (Extira®, CMI, Chicago, Ill.) and the other nine replicates have artificial nest sites made from new pine laminates (Acosta and Sons, Inc., Waterford, Calif.). Over a four week period, 47,900 female bees (and approximately twice as many males) are introduced into the screenhouse beginning on April 8, where thousands of untreated artificial cavities are available for bees in a few large shelters along with the small experimental nesting sites. The Synthetic Blend at 10 CE or 100 CE, filtered cocoon extract at 10.4 CE (prepared as described above), and the negative control are applied to the front of the artificial nest sites only on April 8. Completed nests are counted twice per week. Three of the twelve replicates do not have any completed nests and are removed from the statistical analysis. No significant difference by two-way ANOVA for completed nests exists (F=1.31, df=3.24, P=0.29). However, one-tailed t-test assuming unequal variance comparing the negative control with the Synthetic Blend 100 CE shows significantly more nests are made in the artificial nest sites treated with Synthetic Blend 100 CE (t=2.23, df=9, P=0.026). See Table 6.

The number of cells with female offspring and total cells completed echo the results for completed nests. No significant differences are found among treatments using ANOVA, but a t-test comparing the negative control and Synthetic Blend 100 CE treatment show a significant difference for both cells (t=2.19, df=10, P=0.026) and female offspring (t=2.21, df=10, P=0.026). See Table 6.

TABLE 6

| Ballico screenhouse experiment | Nests/replicate | Cells/replicate |
|---|---|---|
| Synthetic Blend (10 CE) | 5.77 ± 2.93 | 40.8 ± 21.0 |
| Synthetic Blend (100 CE) | 6.22 ± 2.09 | 40.2 ± 12.1 |
| Cocoon Extract (10.4 CE) | 3.22 ± 1.51 | 30.0 ± 12.2 |
| Negative Control | 1.44 ± 0.47 | 12.0 ± 4.2 |

In Lost Hills, two 5-acre screenhouses are used to test Synthetic Blend at 10 CE or 100 CE, filtered cocoon extract at 10.4 CE (prepared as described above), and the negative control applied onto the front of the artificial nest sites. Each screenhouse has thirty-six replicates of each treatment (total 144 artificial nest sites in each screenhouse). Each artificial nest site is a plastic corrugated box with paper tubes for nesting and is attached to a wood post (spaced 35 feet from other posts). Synthetic Blend at 10 CE or 100 CE, filtered cocoon extract at 10.4 CE, and the negative control are applied to the front of the artificial nest sites on the same day as the bees are introduced. The most nests are completed in artificial nest sites onto which Synthetic Blend 100 CE is applied, however, there was no statistically significant difference among treatments (F=1.23, df=3.140, P=0.30). See Table 7.

TABLE 7

| Lost Hills screenhouse experiment | Nests/replicate |
|---|---|
| Synthetic Blend (10 CE) | 3.25 ± 1.12 |
| Synthetic Blend (100 CE) | 4.30 ± 1.42 |
| Cocoon Extract (10.4 CE) | 4.19 ± 1.13 |
| Negative Control | 1.67 ± 0.55 |

Although the results are not definitive in the screenhouses, there is a strong indication that the Synthetic Blend 100 CE increases nesting. In Ballico, the Synthetic Blend 100 CE treatment increases completed nests by 4.3 fold and in Lost Hills, it increases nests by 2.6 fold compared to the negative controls.

Experiment 4. Field Trials of Components of Synthetic Blend

To better understand whether some or all components in Synthetic Blend attract bees, field trials are performed to compare bee response to Synthetic Blend, a mixture of the free fatty acids, and a mixture of the wax esters. The fatty acids decanoic acid, dodecanoic acid, and tetradecanoic acid, purchased from the same suppliers as in Example 3, are mixed by Suterra with ethyl alcohol (the solvent or carrier) (Equistar Chemicals, LP, product SDA40B/200PF/DNB TBA/147600, Houston, Tex.) so that the proportion of the chemicals are similar to amount per cocoon. Similarly, the wax esters hexyl decanoate and decyl dodecanoate, obtained as in Example 3, are mixed by Suterra with ethyl alcohol (the solvent or carrier) (Equistar Chemicals, LP, product SDA40B/200PF/DNB TBA/147600, Houston, Tex.) so that the proportion of the chemicals are similar to amount per cocoon. The mixtures of chemicals are placed into aerosol cans. The spray nozzle for the fatty acid mixture and the wax ester mixture is calibrated to emit 50 CE of the mixture with a single activation. Ethanol is used as a negative control.

In an almond orchard, small, corrugated plastic box shelters (20×23×20 cm) are hung in trees 1 to 2 m from the ground with one bundle of 40 paper tubes per plastic box (artificial nest site). Each tube is lined with a white paper straw. Backings are made by applying gaffers tape to the ends of the nests, pouring clean sand in the nests, and then pouring out the excess sand. The fronts of the artificial nest site are spray painted with flat black paint. Shelters opened in the southeast direction. A randomized complete block design is used with artificial nest sites blocked in 8 groups with 5 trees (3 in one row and 2 in an adjacent row), and blocks are separated by at least 150 feet. Ethyl alcohol at 100 CE (negative control), cocoon extract at 100 CE or 200 CE (positive control), fatty acids mixture at 100 CE, or wax esters mixture 100 CE are sprayed on the front of the paper tubes in an artificial nest site at a distance of 5 cm (+/−0.6 cm) on February 16. Evaporation tests indicate that at most, 2.5% of the material would evaporate in this time period. *O. lignaria* females along with males are released as emerged adults nearby. 80% of the females are released on February 23, and releases are complete by February 26. Females resting in holes are counted at night five times between February 25 and March 16, and completed nests are counted four times during the same time period. Completed nests are x-rayed in July, and the number of cells in each nest is counted.

The establishment of females is low overall in this experiment and for this orchard in general (see Table 8). Artificial nest sites with the negative control or the wax ester mixture at 100 CE have the least number of resting females per observation (0 to 1 female and 1 to 2 females per observation, respectively). Artificial nest sites with the cocoon extract at 200 CE or the fatty acid mixture at 100 CE have the most resting females per observation (2 to 5 females and 3 to 5 females per observation, respectively) (see Table 8 for mean (±SE) number of *O. lignaria* females for five observations). Only 14 nests are completed in this experiment, so no statistical analysis is performed (see Table 8 for mean number (±SE) of nests completed). However, the best performing attractants for completed nests and completed cells are the cocoon extract at 200 CE and the fatty acids mixture at 100 CE (see Table 8 for mean number (±SE) of cells completed).

TABLE 8

| Almond Orchard | Females/date | Nests/replicate | Cells/replicate |
|---|---|---|---|
| Cocoon extract (100 CE) | 2.0 ± 0.71 | 0.13 ± 0.13 | 0.38 ± 0.47 |
| Cocoon extract (200 CE) | 3.2 ± 0.49 | 0.63 ± 0.32 | 3.00 ± 2.85 |
| Fatty acids mixture (100 CE) | 3.6 ± 0.89 | 0.86 ± 0.38 | 3.75 ± 3.41 |
| Wax esters mixture (100 CE) | 1.6 ± 0.40 | 0.25 ± 0.25 | 1.25 ± 1.56 |
| Negative control | 0.4 ± 0.25 | 0 | 0 |

In an apple orchard, an experiment is conducted to compare the attractant capabilities of Synthetic Blend at 100 CE or 200 CE, the fatty acids mixture at 100 CE or 200 CE, the wax esters mixture at 100 CE or 200 CE, and the negative control. Artificial nest sites of small, corrugated plastic box shelters are hung in apple trees 1 to 2 m from the ground, each containing two bundles of 21 paper tubes. Each paper tube is lined with a white paper straw and plugged with a plastic stopper. Artificial nest sites open in the southeast direction. A randomized complete block design is used with artificial nest sites blocked in 4 groups with 7 trees (4 boxes in one row and 3 in an adjacent row) and blocks are separated by at least 2 rows of trees. The fronts of the paper tubes are sprayed with either Synthetic Blend at 100 CE or 200 CE, the fatty acids mixture at 100 CE or 200 CE, the wax esters mixture at 100 CE or 200 CE, or the negative control at 100 CE from a distance of approximately 4 cm on the day before the artificial nest sites are placed in the orchard (placement occurs on April 23). Also on April 23, *O. lignaria* females and males are allowed to emerge from dark emergence boxes spaced evenly between treatment blocks. Female bees resting in holes are counted in the early morning (at approximately 0700 h) on Mondays, Wednesdays, and Fridays throughout the study period (April 25 through May 16); artificial nest sites are checked for completed (plugged) nests daily. Once per week, plugged nests are removed and replaced with a tube to which the same treatment is applied on the same day as replacement. All artificial nest sites are removed from the orchard and stored outdoors. Artificial nest sites are x-rayed in June, and the number of cells in each nest is recorded.

For this experiment, the establishment of *O. lignaria* females is good, with most females present in the second and third weeks of observations. The most females (mean (±SE) for 10 sample dates) are present in the artificial nest sites treated with the fatty acids mixture at 200 CE (range=2-22), followed by artificial nest sites treated with Synthetic Blend at 100 CE or Synthetic Blend at 200 CE (range=1-20 for each) (see Table 9). The fewest females are found in the artificial nest sites treated with the wax ester mixtures at 100 CE and the wax ester mixture at 200 CE (range=0-14 for each), and artificial nest sites treated with the negative control harbored an intermediate number of females bees (range=3-14). Table 9 also provides the mean number (±SE) of nests for four replicates and the mean (±SE) number of cells for four replicates for this experiment. Generalized linear mixed model (GLMM) analysis shows a significant effect of treatment and date on the number of bees present (treatment: F=10.92, df=6.54, P<0.0001; date: F=13.06, df=9.54, P<0.0001). Tukey's test shows that Synthetic Blend and the fatty acids mixture are significantly better attractants than the wax esters mixture, and that Synthetic Blend at 100 CE and the fatty acids mixture at 200 CE are significantly better attractants than the negative control.

TABLE 9

| Apple Orchard | Females/date | Nests/replicate | Cells/replicate |
| --- | --- | --- | --- |
| Synthetic Blend (100 CE) | 12.3 ± 2.01 | 7.0 ± 3.03 | 37.8 ± 17.35 |
| Synthetic Blend (200 CE) | 10.8 ± 2.03 | 9.0 ± 4.24 | 28.5 ± 12.92 |
| Fatty acids mixture (100 CE) | 9.4 ± 1.71 | 6.0 ± 2.04 | 27.5 ± 9.11 |
| Wax esters mixture (100 CE) | 3.8 ± 0.74 | 2.0 ± 0.71 | 6.5 ± 2.40 |
| Fatty acids mixture (200 CE) | 13.4 ± 1.87 | 12.8 ± 3.92 | 50.3 ± 16.05 |
| Wax esters mixture (200 CE) | 6.9 ± 1.44 | 2.5 ± 1.85 | 8.8 ± 6.79 |
| Negative control | 8.3 ± 1.46 | 4.3 ± 3.60 | 21.8 ± 17.49 |

Example 5

Evaporation Rates of Attractants

Figure 2:
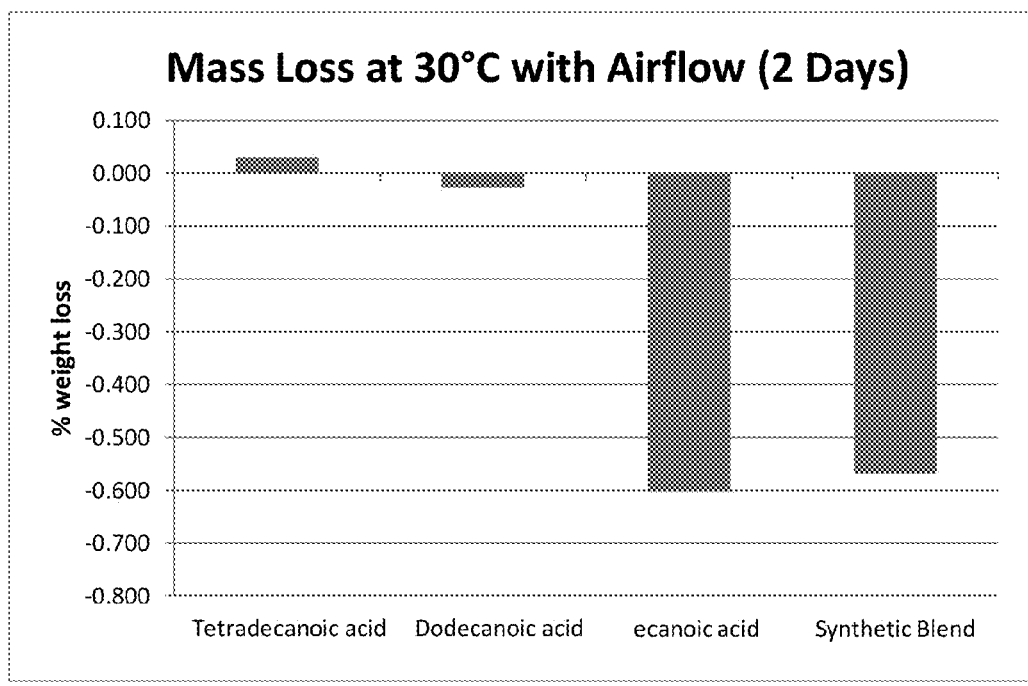
FIG. 2 shows the percentage loss of mass via evaporation of tetradecanoic acid, dodecanoic acid, decanoic acid, and Synthetic Blend when exposed to airflow for two days at 30° C.
Figure 3:
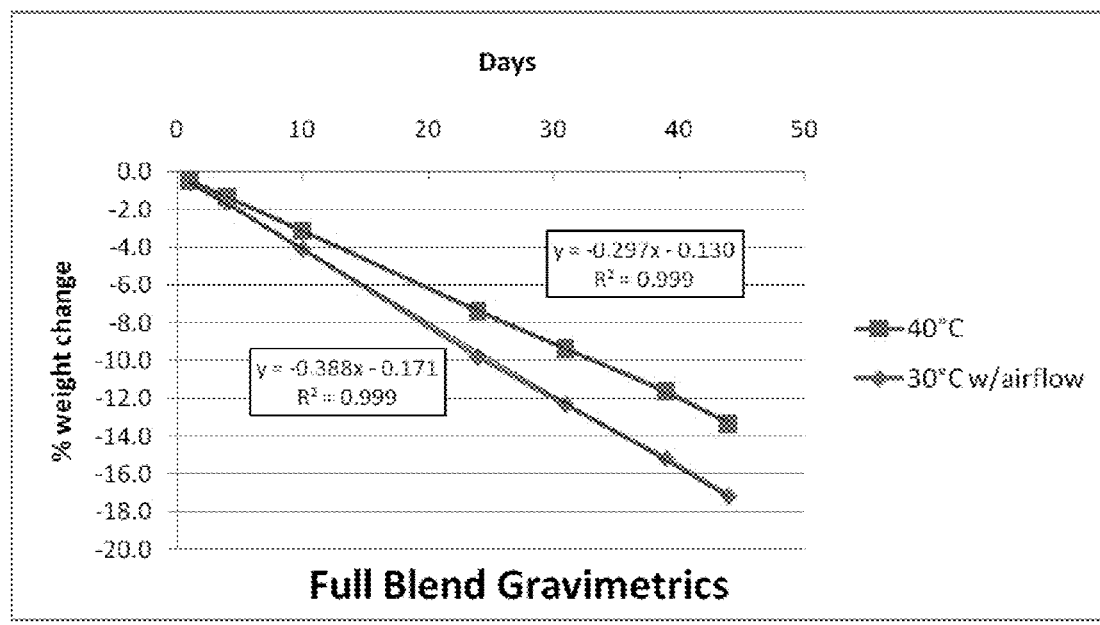
FIG. 3 shows the linear relationship between the percentage weight loss of Synthetic Blend and number of days of exposure at 30° C. with air flow and at 40° C. without air flow.

The objective of this experiment is to quantify the loss of the fatty acids and Synthetic Blend via evaporation. Synthetic Blend is prepared as per Example 3. Decanoic acid, dodecanoic acid, and tetradecanoic acid are purchased as per Example 4. Synthetic Blend is a liquid at room temperature. Vials containing between 0.235 and 0.304 grams of either Synthetic Blend or each individual fatty acid are placed in a 40° C. incubator and a ~30° C. incubator room with a fan and are weighed after 1, 4, 10, 24, 31, 39 and 44 days. Three vials are monitored for each attractant, and the average weight loss is calculated. All samples lose weight faster at 30° C. with airflow compared to 40° C. without airflow. After 2 days at 30° C. with airflow, Synthetic Blend loses only 0.57% of its weight (see FIG. 2). This loss of mass is caused mostly by evaporation of decanoic acid which comprises approximately 73% of Synthetic Blend. After 24 days, Synthetic Blend loses 9.8% of its mass and after 44 days, 17.2% of its mass. A linear relationship is found between weight loss and days for both environments (see FIG. 3).

In order for the attractant to effectively induce female bees to nest at the site or area containing the attractant, a sufficient amount of the attractant must persist while the female bees are establishing nests, or one should reapply the attractant, as necessary, during that time period. A typical orchard that is to be pollinated by *Osmia* spp. blooms for three to four weeks, on average. Synthetic Blend has a slow evaporation rate with respect to the expected field conditions it will encounter. After 2 weeks one could expect, at most, a loss of 5.3% of the material, and it would take 129 days for half of the material to evaporate. The composition of the blend will change over time as decanoic acid evaporated much faster than tetradecanoic acid and dodecanoic acid.

Example 6

Electroantennal Response of *O. lignaria* Female Antennae to Attractants

The objective of this experiment is to compare *O. lignaria* antennal response to Synthetic Blend, fatty acids mixture, wax esters mixture, and ethyl alcohol (Equistar Chemicals, LP, Houston, Tex.) (the solvent or carrier). Female and male bees are maintained in laboratory cages and feed on honey-water ad libitum for four days. On the fourth day, one antenna at a time is removed from each chilled, live female test bee with scissors and placed on the electrode holder of a Syntech electroantennograph (EAG) probe (Kirchzarten, Germany). The EAG probe is inserted into a glass tube into which flows humidified air, and into which a stimulus (the attractant) is applied.

A Syntech programmable stimulus controller (Kirchzarten, Germany) is used to puff air through a disposable glass pipette (14.6 cm) into the glass tube containing the antenna. Air serves as a control. The Synthetic Blend, fatty acids mixture, wax esters mixture, or ethyl alcohol (Equistar Chemicals, LP, Houston, Tex.) is sprayed on circular filter paper in a glass Petri dish (9 cm) at a dose of 100 CE (except for the ethyl alcohol which is applied at the same rate as the Synthetic Blend). The dose is given in 2 activations (50 CE each) from the aerosol can at 4 cm distance onto the filter paper in two spots. From the center of where the two spots connected, a 1.5 cm$^2$ piece of filter paper is cut from the larger filter paper circle. The piece of filter paper is placed into the disposable glass pipette that is used for delivery by applying a controlled puff of air over the filter paper. Air, ethyl alcohol, Synthetic Blend, fatty acids mixture and wax esters mixture are delivered in succession every minute until an antenna is exposed to each cue five times and to the air six times (total test period=26 minutes). The antennal responses are recorded, and their amplitudes are measured using Syntech EAG software (Kirchzarten, Germany).

The antennal responses of twenty female bees are recorded, with eighteen of those bees having both right and left antennae tested in alternating order. The responses to Synthetic Blend and the fatty acids mixture are higher than to the wax esters mixture, ethyl alcohol, and air (see Table 10).

GLMM analysis reveals that the differences are significant for the effect of the chemicals on the response amplitudes (F=43.85, df=4.981, P<0.0001), but that there are no differences in the responses between the right and left antennae (F=0.95, df=1.981, P=0.3310) nor to the order in which the antennae from the same bee are tested (F=2.69, df=1.981, P=0.1016).

TABLE 10

| Stimulant | No. responses | Mean Amplitude |
|---|---|---|
| Air | 228 | −0.81 ± 0.03 |
| Wax Esters Mixture (100 CE) | 191 | −0.85 ± 0.04 |
| Fatty Acids Mixture (100 CE) | 189 | −1.36 ± 0.05 |
| Synthetic Blend (100 CE) | 190 | −1.30 ± 0.04 |
| Ethyl Alcohol | 190 | −0.84 ± 0.04 |

EAG responses to the attractants mirror the bees' responses during the orchard nesting experiments. *O. lignaria* females have a greater response to the fatty acids mixture (attractant) and Synthetic Blend than to the wax esters mixture or ethyl alcohol (the solvent or carrier).

Example 7

Electroantennal Responses of *O. Lignaria* Females to Certain Fractions of the Cocoon Extract In two simple but inconclusive laboratory and field trials (not discussed here), Fractions 1, 8, and 9 of the cocoon extract (see Table 1) are attractive to *O. lignaria* females in some instances. The objective of this example is to screen these fractions for compounds that may be important attractants but were overlooked previously. Therefore, studies are performed between April and May of 2013 at the North Dakota State University. Fractions 1, 8, and 9 are HPLC-purified for testing on female bees reared in California and shipped as cocooned adults to North Dakota in the winter. Female bees emerge from the cocoon after incubation at 25° C. They are placed in a small laboratory cage (0.03 m$^3$) and given 10% sugar water ad libitum. Two day old females are chilled, and one antenna is excised using a micro scissors (the second antenna remained on the bee until needed). The distal end of the antenna also is excised, and the antenna is placed into the antennal holder. The holder is constructed of Plexiglass to hold the two electrodes and provide an area for a gold wire and the antenna to make contact. The gold wire ends in a small cavity that is filled with electrode gel.

Gas chromatography-flame ionization detection: electroantennographic detection (GC-FID:EAD) (Syntech, Kirchzarten, Germany) analyses are carried out using a Varian 3800 gas chromatograph fitted with a zb-5 column (30 m×0.25 mm inner diameter, 0.25 μm film thickness) using hydrogen carrier gas (2 ml/min), and a 1:3 (FID:EAD) split ratio. Fractions are injected into the GC at 0.02 CE. The behavioral response of each fraction is tested on a fresh antenna between 25 and 35 times, and the results of the most responsive tests are averaged.

Figure 4:
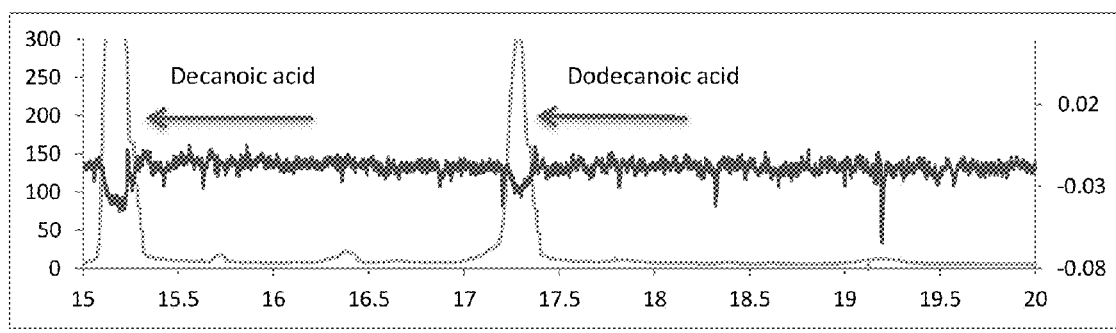
FIG. 4 shows the averaged gas chromatography-flame ionization detector and averaged electroantennographic detector (GC-FID:EAD) results for Fraction 9 over the time period when two peaks, identified as decanoic acid and dodecanoic acid, elute. Antennal responses to these fatty acids are indicated by the dip in the EAD chromatogram superimposed over the FID chromatogram.

GC-FID:EAD analysis results in two peaks eliciting responses in more than 50% of the tests (see FIG. 4). These two peaks, both found in Fraction 9, show a consistency not seen with the other fractions. The two peaks are later identified by GC-MS as decanoic acid and dodecanoic acid. No unique components of Fractions 1 and 8 produce antennal responses from *O. lignaria* females.

Example 8

Electroantennal Response of Female *O. Lignaria*, *O. Bucephala*, and *O. Cornifrons* Antennae to Specific Fatty Acids The objective of this example is to compare antennal responses of three *Osmia* species (*O. lignaria, O. bucephala,* and *O. cornifrons* obtained from near a Pennsylvania apple orchard) to each of three fatty acids, each combined mixture of two acids, and the combined mixture of all acids (see Table 11). Female and male bees are maintained in laboratory cages and fed honey-water ad libitum for four days. On the fourth day, one antenna at a time is removed from each chilled, live female test bee with scissors and placed on the electrode probe of a Syntech EAG (Kirchzarten, Germany). The electrode with the antenna is inserted into a glass tube into which flows humidified air, and into which a stimulus (air, a fatty acid, or fatty acid mixture) is applied.

TABLE 11

| Single Attractant Chemical | Combined Attractant Chemicals |
|---|---|
| Decanoic acid | Decanoic and dodecanoic acids |
| Dodecanoic acid | Decanoic and tetradecanoic acids |
| Tetradecanoic acid | Dodecanoic and tetradecanoic acids |
| Air (negative control) | Decanoic, dodecanoic, and tetradecanoic acids |

Each of the above indicated fatty acids, purchased from Sigma-Aldrich (St. Louis, Mo.), are dissolved in ethyl alcohol at a concentration similar to that used for the Synthetic Blend. Each fatty acid and each mixture (Equistar Chemicals, LP, Houston, Tex.) is evenly applied to a circular filter paper in Petri dish (9 cm) at dose of 100 CE. A 1.5 cm$^2$ piece of filter paper is cut from the center of the filter paper circle. The piece of filter paper is placed into the disposable glass pipette (4.6 cm) that is used for delivery by applying a controlled puff of air over the filter paper.

Each of the single or mixtures of fatty acids described above (see Table 11) and a control (air) are tested on an antenna: Air or filter paper pieces with each fatty acid or fatty acids mixture are delivered in succession every minute until an antenna is exposed to each cue and air three times (total test period=30 minutes). The antennal responses are recorded, and their amplitudes are measured using Syntech EAG software (Kirchzarten, Germany). The antennal responses of ≤12 female bees per species are recorded. Data are square root transformed for a normal distribution before responses are compared for the effects of species, the compounds tested, and the repeated effect of occurrence (when stimulus is delivered from first to third series in the sequence) for each within test replicate using PROC MIXED in SAS 9.2 (Version 9.2, SAS Institute Inc., North Carolina). Random effects included in the model are sample and whether the antenna is on the left or right side of the head. Tukey's test is applied for posthoc comparison of significant effects.

Analysis reveals significant differences in antennal responses by species (F=6.27, df=2.29, P=0.006), occurrence of the stimulus (F=4.09, df=2.464, P<0.017), the compounds tested (F=137.44, df=7.203, P<0.0001), as well as for the interaction of species and occurrence of the stimulus (F=8.85, df=4.464, P<0.0001) and the interaction of species by compound tested (F=3.61, df=14.203, P<0.0001). The antennal responses of *O. lignaria* are significantly lower than those of *O. bucephala* (t=3.06, df=29, adjusted P=0.013), but they are not significantly different than antennal responses of *O. cornifrons* (t=0.22, df=29, adjusted P=0.974). The antennal responses of *O. cornifrons* also are significantly lower than those of *O. bucephala* (t=3.26, df=29, adjusted P=0.008). The response at the first occurrence of the stimulus is significantly different from the last (third) occurrence (t=2.67, df=464, adjusted P=0.021), and shows decreased sensitivity of antennae over time as expected. Response to decanoic acid is significantly different from air and all other single fatty acids or their mixtures. The response to air is significantly lower than the response to all other stimuli, except for the dodecanoic acid and tetradecanoic acid mixture. The combination of all three fatty acids is significantly different from (greater or less than) all other stimuli, except for the decanoic acid and dodecanoic acid mixture. The response to dodecanoic acid is significantly less than the response to the mixtures of decanoic acid and dodecanoic acid, decanoic acid and tetradecanoic acid, and dodecanoic acid and tetradecanoic acid. The response to tetradecanoic acid does not significantly differ from the response to dodecanoic acid or the dodecanoic acid and tetradecanoic acid mixture. Overall, decanoic acid elicits the greatest antennal responses, and mixtures containing decanoic acid plus one of the other fatty acids, but not both, also stimulate antennae more than does air.

TABLE 12

| Compounds used as Attractant | *O. lignaria* (n = 12) Mean Amplitude ± SE | *O. cornifrons* (n = 12) Mean Amplitude ± SE | *O. bucephala* (n = 8) Mean Amplitude ± SE |
|---|---|---|---|
| Air (negative control) | −0.49 ± 0.04 | −0.47 ± 0.04 | −0.98 ± 0.06 |
| Decanoic, dodecanoic, and tetradecanoic acids | −0.57 ± 0.04 | −0.55 ± 0.05 | −1.03 ± 0.08 |
| Decanoic and dodecanoic acids | −0.63 ± 0.05 | −0.57 ± 0.05 | −1.08 ± 0.08 |
| Decanoic and tetradecanoic acids | −0.80 ± 0.06 | −0.76 ± 0.05 | −1.19 ± 0.09 |
| Dodecanoic and tetradecanoic acids | −0.47 ± 0.04 | −0.45 ± 0.04 | −0.96 ± 0.08 |
| Decanoic acid | −0.98 ± 0.06 | −0.89 ± 0.06 | −1.31 ± 0.10 |
| Dodecanoic acid | −0.41 ± 0.03 | −0.43 ± 0.04 | −0.83 ± 0.06 |
| Tetradecanoic acid | −0.41 ± 0.03 | −0.43 ± 0.04 | −0.92 ± 0.07 |

Example 9

Field Tests with Fatty Acids

To better understand whether application of one, or some mixture of, free fatty acids to nesting material or artificial nest sites is attractive to *O. lignaria*, two experimental sets are generated so that one set tests for differences in bee response to each single fatty acid and the other set tests for differences in bee response to mixtures of the fatty acids described above in Table 11. Fatty acids are applied to separate filter papers so that each filter paper contains 200 CE. As a negative control, the volume of ethyl alcohol used for the other samples is applied to its own filter paper. For the experiment in an apple orchard in Utah, each small, corrugated plastic box artificial nest site (20×23×20 cm), with two bundles of 19 paper tubes each, is hung in an apple tree; nest sites are separated by one tree between them within each replicate group. To each nest site, two of the 200 CE impregnated filter papers are applied; thus, a total of 400 CE of the stimulus is present within each nest site. Each filter paper (containing either a single fatty acid, one mixture of fatty acids, or the negative control) is attached using cable ties to the front of one tube in each of the two bundles in each artificial nest site. The filter papers are replaced weekly. Each artificial nest site contains only one type of treatment. For the single fatty acid comparison, artificial nest sites are placed in the orchard in five replicates of the three treatments plus a control (i.e., four nest sites per replicate), with each artificial nest site opening facing southeast. For the mixtures of fatty acids comparison, artificial nest sites are placed in the orchard in five replicates of the four treatments plus a control (i.e., five nest sites per replicate), with each artificial nest site opening facing southeast. Both experimental sets are located in the same orchard where they are intermittently placed but separated by at least two rows of apple trees. A total of 540 female and 1000 male bees are released throughout the orchard at least one tree row from the artificial nest sites using several release box sites (with equal numbers of bees per box). Artificial nest sites are checked daily for the presence of male and female bees and for tubes with completed nests. Tubes with completed nests are removed and are replaced with fresh ones. Later, all nests containing any bee cells are examined with x-radiography to determine number of cells in each nest.

TABLE 13

| Compounds Used as Cue | Females/date | Nests/replicate | Cells/replicate |
|---|---|---|---|
| Decanoic acid | 10.2 ± 1.14 | 2.6 ± 1.17 | 13.4 ± 6.13 |
| Dodecanoic acid | 3.4 ± 0.67 | 1.4 ± 1.17 | 8.8 ± 7.40 |
| Tetradecanoic acid | 0.4 ± 0.17 | 0.2 ± 0.2 | 1.6 ± 1.6 |
| Control (Ethanol) | 3.7 ± 0.99 | 0.4 ± 0.4 | 2.2 ± 2.2 |

TABLE 14

| Compounds Used as Cue | Females/date | Nests/replicate | Cells/replicate |
|---|---|---|---|
| Decanoic, dodecanoic, and tetradecanoic acids | 2.1 ± 0.60 | 1.0 ± 0.77 | 3.8 ± 2.46 |
| Decanoic and dodecanoic acids | 8.7 ± 2.63 | 2.2 ± 1.56 | 9.6 ± 6.28 |
| Decanoic and tetradecanoic acids | 14.0 ± 2.45 | 1.0 ± 0.55 | 7.0 ± 3.38 |
| Dodecanoic and tetradecanoic acids | 1.3 ± 0.35 | 0.4 ± 0.24 | 1.4 ± 1.17 |
| Control (Ethanol) | 1.2 ± 0.34 | 0 | 0 |

For the two experiment sets, most females (mean number (±SE) of *O. lignaria* females for 9 sample dates) are found in the artificial nest sites treated with decanoic acid (range=4-15), a mixture of decanoic acid and tetradecanoic acid (range=1-24), and a mixture of decanoic acid and dodecanoic acid (range=0-22) (see Tables 13 & 14 above). The fewest females are found in the artificial nest sites treated with tetradecanoic acid (range=0-1) in the first experiment set and the control for the second set (range=0-3). Tables 13 & 14 also provide the mean number (±SE) of nests for five replicates and the mean (±SE) number of cells for five replicates for these experiment sets. The same trends as above apply to the nests and cells produced. Because many sites contained no bees or nests, statistical evaluation of differences in the number of females present in nests and the number of nests and cells produced could not be performed.

*Osmia lignaria* females appear to be more likely to nest where decanoic acid is present compared to where dodecanoic acid is present. Nonetheless, the presence of dodecanoic acid at nest sites result in more cells being produced in those sites compared to sites with tetradecanoic acid. No additive or synergistic effect of any mixture of two or three of the fatty acids tested is found. The lower doses of dodecanoic and tetradecanoic acids, based on the amount in one cocoon, may have made them less effective in attracting bees than if they had been presented at the same dose as was decanoic acid.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference. Recitation of ranges of values herein are merely intended to serve as a shorthand method of referring individually to each separate value falling within the range, unless otherwise indicated herein, and each separate value is incorporated into the specification as if it is individually recited herein. For example, if the range 10-15 is disclosed, then 11, 12, 13, and 14 are also disclosed. All numeric values provided herein include a 10% increase and a 10% decrease of that value. So, "ten" includes all numbers between "nine" and "eleven"; "one hundred" includes all numbers between "ninety" and "one-hundred ten". "Approximately ten" includes all numbers between "nine" and "eleven".

We, the inventors, claim:

1. A method for attracting *Osmia* spp. bees to a nesting structure, a nest site, or an area for nesting comprising applying to said nesting structure, said nest site, or said area for nesting an effective amount of a nesting attractant to attract said *Osmia* spp. bees to said nesting structure, said nest site or said area for nesting wherein said nesting attractant is selected from the group consisting of decanoic acid, dodecanoic acid, tetradecanoic acid, a combination of any two thereof, and a combination of all three thereof; and optionally a carrier.

2. The method of claim 1 wherein said *Osmia* spp. bee is selected from the group consisting of *O. lignaria, O. cornifrons, O. bucephala, O. aglaia, O. ribifloris, O. bruneri, O. cornuta*, and *O. bicornis*.

3. The method of claim 1 wherein said carrier comprises ethyl alcohol.

4. The method of claim 1 wherein said effective amount of said decanoic acid is between approximately 11 mg and approximately 110 mg, said effective amount of said dodecanoic acid is between approximately 11 mg and approximately 110 mg, and said effective amount of said tetradecanoic acid is between approximately 11 mg and approximately 110 mg.

* * * * *